(12) United States Patent
Ogasawara

(10) Patent No.: US 7,750,057 B2
(45) Date of Patent: Jul. 6, 2010

(54) METHOD FOR OBTAINING ALKALI METAL SALT AQUEOUS SOLUTION OF AROMATIC DIHYDROXY COMPOUND FROM WASTE AROMATIC POLYCARBONATE

(75) Inventor: Kazuyoshi Ogasawara, Chiyoda-ku (JP)

(73) Assignee: Teijin Chemicals, Ltd., Tokyo (JP)

( * ) Notice: Subject to any disclaimer, the term of this patent is extended or adjusted under 35 U.S.C. 154(b) by 213 days.

(21) Appl. No.: 11/918,891

(22) PCT Filed: Apr. 20, 2005

(86) PCT No.: PCT/JP2005/007941

§ 371 (c)(1),
(2), (4) Date: Oct. 19, 2007

(87) PCT Pub. No.: WO2006/114893

PCT Pub. Date: Nov. 2, 2006

(65) Prior Publication Data

US 2009/0170969 A1    Jul. 2, 2009

(51) Int. Cl.
*C08J 11/04* (2006.01)
(52) U.S. Cl. .................. 521/40; 521/40.5; 525/488; 525/489; 568/724
(58) Field of Classification Search .................. 521/40, 521/40.5, 41, 41.5, 47, 48, 60; 528/271, 528/272, 488, 489, 491; 568/724
See application file for complete search history.

(56) References Cited

U.S. PATENT DOCUMENTS

| 4,212,774 A | * | 7/1980 | Idel | 521/40 |
| 4,885,407 A | * | 12/1989 | Fox et al. | 568/724 |
| 5,391,802 A | | 2/1995 | Buysch et al. | |

FOREIGN PATENT DOCUMENTS

| EP | 0 355 319 | 2/1990 |
| JP | 40-16536 | 7/1965 |
| JP | 54-48869 | 4/1979 |
| JP | 6-56985 | 3/1994 |
| JP | 10-259151 | 9/1998 |
| JP | 2001-160243 | 6/2001 |
| JP | 2001-302844 | 10/2001 |
| JP | 2002-212335 | 7/2002 |
| JP | 2005-126358 | 5/2005 |

OTHER PUBLICATIONS

Supplementary European Search Report issued Apr. 25, 2008 in the International (PCT) Application of which the present application is the U.S. National Stage.

* cited by examiner

*Primary Examiner*—Ling-Siu Choi
*Assistant Examiner*—Frances Tischler
(74) *Attorney, Agent, or Firm*—Wenderoth, Lind & Ponack, L.L.P.

(57) ABSTRACT

There is provided a method for obtaining an aqueous solution of an alkali metal salt of an aromatic dihydroxy compound by decomposing a waste aromatic polycarbonate by an alkali metal hydroxide aqueous solution. The method comprises (1) a dissolution step of dissolving a waste aromatic polycarbonate in a chlorinated hydrocarbon solvent, (2) a decomposition step of adding an alkali metal hydroxide aqueous solution to this solution to decompose the aromatic polycarbonate, (3) a re-dissolution step of adding water to this decomposed solution to dissolve a solid, (4) a two phase formation step of leaving the treated solution obtained in the step (3) to stand to form an organic solvent phase (organic phase) and an aqueous solution phase (aqueous phase), and (5) a separation/collection step of separating the aqueous phase from the organic solvent phase and collecting the aqueous phase.

16 Claims, No Drawings

METHOD FOR OBTAINING ALKALI METAL SALT AQUEOUS SOLUTION OF AROMATIC DIHYDROXY COMPOUND FROM WASTE AROMATIC POLYCARBONATE

FIELD OF THE INVENTION

The present invention relates to a method for obtaining an alkali metal salt aqueous solution of an aromatic dihydroxy compound by decomposing a waste aromatic polycarbonate by a metal hydroxide aqueous solution and a method for collecting the aromatic dihydroxy compound from the aqueous solution. Further, the present invention also relates to an aromatic polycarbonate production method using the alkali metal salt aqueous solution of the aromatic dihydroxy compound or the collected aromatic dihydroxy compound in a polycarbonate production process.

BACKGROUND ART

An aromatic polycarbonate (hereinafter may be abbreviated as "PC") has excellent mechanical properties, electric properties, heat resistance, cold resistance and transparency and is a material which is used in various applications including lenses, optical disks such as compact disks, building materials, automotive parts, chassis for office automation equipment and camera bodies, and demand therefor has been increasing every year. The amount of PC products discarded increases along with an increase in demand for PCs, and most of them are dealt with by a method such as incineration or burying in the ground. Thus, the increase in demand for PCs accelerates not only depletion of oil resources but also deterioration of the global environment. Consequently, recycling of waste plastic has become important.

As a method for recycling waste plastic, (1) thermal recycling which comprises recovering waste plastic as thermal energy, (2) material recycling which comprises mixing waste plastic with new plastic or plastic of another kind in a given ratio and processes the plastic mixture into a product and (3) chemical recycling which comprises chemically decomposing waste plastic into a raw material for plastic and reusing it in production of plastic are primarily used. However, the thermal recycling essentially destroys the global environment and decreases resources since it produces carbon dioxide and water when burning plastic and recovering heat. The material recycling is environmentally desirable since it imposes the least burden on the environment in terms of consumption of resources. However, products which can be mixed with waste plastic are limited, the amount of waste plastic which can be mixed into a product is small, and the amount of waste plastic which can be recycled is limited. The chemical recycling is an industrially useful recycling method since it decomposes plastic into a raw material which can be directly used in production of plastic.

As a method of chemically recycling a PC, a method comprising decomposing the PC with an excessive alkali metal salt aqueous solution followed by neutralization to collect an aromatic dihydroxy compound has been known. In JP-B 40-016536, a PC and a 1 to 30% alkali aqueous solution are charged into a pressure-resistant container to hydrolyze the PC at 100° C. or higher, preferably 150° C. or higher, and the obtained hydrolysate is made acidic, dissolved in methanol and subjected to an activated carbon treatment to remove coloring components followed by reprecipitation to obtain white bisphenol. JP-A 54-048869 discloses a method comprising saponifying polycarbonate scraps in bulk or as a solution, separating unsaponified components, phosgenating the saponified mixture and using the resulting product in a polycarbonate polymerization process totally without purification and treatment processes. JP-A 6-056985 discloses a method comprising decomposing a PC with phenol in the presence of an alkali catalyst to collect an aromatic dihydroxy compound and a diaryl carbonate. Further, JP-A 10-259151 discloses a method comprising carrying out a transesterification reaction in a toluene, xylene, benzene or dioxane solvent by use of a small amount of an alkali as a catalyst to obtain a dialkyl carbonate and an aromatic dihydroxy compound. Further, JP-A 2002-212335 proposes a method comprising carrying out transesterification of PC and lower alcohol in the presence of a solvent such as alkyl chloride, ether or aromatic hydrocarbon solvent and a tertiary amine as a catalyst to obtain an aromatic dihydroxy compound and a dialkyl carbonate.

However, since the method disclosed in JP-B 40-016536 uses the thin alkali aqueous solution, the reaction takes place at high temperatures. Further, since the method uses a very large amount of water in a posttreatment to reprecipitate a yellow coloring component from methanol/water, liquid waste disposal is very complicated. The method disclosed in JP-A 54-048869 uses polycarbonate scraps in a polymerization reaction without a purification process, so that additives, colorants and the like which are used in plastic as nearly essential components are included in the PC production process and affect product quality. The methods disclosed in JP-A 6-056985, JP-A 10-259151 and JP-A 2002-212335 have a complicated step of separating and collecting a decomposition product and a solvent and produce unwanted by-products.

DISCLOSURE OF THE INVENTION

An object of the present invention is to provide a method for obtaining an alkali metal salt aqueous solution of a high-quality aromatic dihydroxy compound suited for a raw material for polycarbonate by processing a waste aromatic polycarbonate at low cost, in a short decomposition time and in large quantity without producing coloring components.

Another object of the present invention is to provide a method for collecting a high-purity aromatic dihydroxy compound from the alkali metal salt aqueous solution of the aromatic dihydroxy compound which has been obtained by decomposition of the waste aromatic polycarbonate.

Still another object of the present invention is to provide a method for producing an aromatic polycarbonate by using the metal salt aqueous solution of the aromatic dihydroxy compound or the collected aromatic dihydroxy compound.

Still another object of the present invention is to provide a method for recycling the aromatic polycarbonate produced by using the alkali metal salt aqueous solution of the aromatic dihydroxy compound obtained by decomposition of the aromatic polycarbonate used in a waste optical disk or the collected aromatic dihydroxy compound as a substrate for an optical disk.

The present inventors have made intensive studies to solve these problems. As a result, they have found that surprisingly, a decomposition reaction proceeds quickly under mild conditions and an alkali metal salt aqueous solution of an aromatic dihydroxy compound which is a product is obtained by preferably using a solvent used in production of an aromatic polycarbonate and an alkali metal hydroxide aqueous solution in proper amounts by a specific process, that a high-quality aromatic dihydroxy compound is obtained by treating the alkali metal salt aqueous solution of the aromatic dihydroxy compound with an acid aqueous solution in the presence of the solvent used in production of the aromatic polycarbonate, and that the quality of an aromatic polycarbonate produced by using the alkali metal salt aqueous solution of the aromatic dihydroxy compound or the aromatic dihydroxy compound as a raw material is equivalent to the quality of an aromatic polycarbonate produced by using a commercially available dihydroxy compound. The present invention has been completed based on these findings.

That is, according to the present invention, the following methods are provided.

(1) A method for obtaining an alkali metal salt aqueous solution of an aromatic dihydroxy compound which constitutes an aromatic polycarbonate by decomposing the waste aromatic polycarbonate by an alkali metal hydroxide aqueous solution, the method comprising:
(a) a step (dissolution step) of dissolving a waste aromatic polycarbonate in a chlorinated hydrocarbon solvent to prepare an organic solvent solution having the aromatic polycarbonate (PC) dissolved therein in a concentration of 8 to 30 wt %,
(b) a step (decomposition step) of adding an alkali metal hydroxide aqueous solution containing 45 to 55 wt % of alkali metal hydroxide to the obtained organic solvent solution to decompose the aromatic polycarbonate at a temperature of 30 to 50° C.,
(c) a step (re-dissolution step) of adding water to the decomposed solution obtained in the step (b) to dissolve an alkali metal salt of an aromatic dihydroxy compound as a solid contained in the decomposed solution in water,
(d) a step (two phase formation step) of leaving the treated solution obtained in the step (c) to stand to form an organic solvent solution phase (organic phase) and an aqueous solution phase (aqueous phase) in the step (d), and
(e) a step (separation/collection step) of separating the aqueous solution phase (aqueous phase) from the organic solvent solution phase (organic phase) and collecting the aqueous solution phase (aqueous phase).

(2) The method of the above (1), wherein the chlorinated hydrocarbon solvent contains at least one solvent selected from the group consisting of dichloromethane, dichloroethane and chloroform in an amount of at least 80 wt %.

(3) The method of the above (1), wherein the alkali metal hydroxide is sodium hydroxide.

(4) The method of the above (1), wherein the aromatic polycarbonate comprises bisphenol A as a main aromatic dihydroxy compound.

(5) The method of the above (1), wherein the organic solvent solution in the dissolution step has the aromatic polycarbonate (PC) dissolved therein in a concentration of 10 to 28 wt %.

(6) The method of the above (1), wherein the alkali metal hydroxide aqueous solution in the decomposition step is an aqueous solution containing 47 to 53 wt % of alkali metal hydroxide.

(7) The method of the above (1), wherein in the decomposition step, the alkali metal hydroxide aqueous solution is used in such an amount that it contains 4 to 8 moles of alkali metal hydroxide per mole of the carbonate linkage of the aromatic polycarbonate.

(8) The method of the above (1), wherein in the decomposition step, the decomposition temperature is a temperature of 30 to 45° C.

(9) The method of the above (1), wherein the waste polycarbonate is an optical disk product formed from a polycarbonate or a material discharged from its production process.

(10) The method of the above (1), wherein in the dissolution step, an antioxidant is added to the organic solvent solution in an amount of 0.05 to 4 parts by weight based on 100 parts by weight of the aromatic polycarbonate.

(11) The method of the above (1), wherein the decomposition step, re-dissolution step and two phase formation step are carried out at least in a non-oxygen gas atmosphere.

(12) The method of the above (1), comprising a step (re-separation/collection step) of adding a chlorinated hydrocarbon solvent to the aqueous solution phase obtained by the separation/collection step to form an organic solvent phase and an aqueous solution phase, separating the aqueous solution phase from the organic solvent phase and collecting the obtained aqueous solution phase.

(13) A method for producing an aromatic polycarbonate which comprises bringing the aqueous solution phase obtained by the separation/collection step of the above (1) into contact with chlorinated hydrocarbon and reacting the phase with phosgene in accordance with an interfacial polymerization process.

(14) A method for producing an aromatic polycarbonate which comprises mixing the aqueous solution phase obtained by the separation/collection step of the above (1) with an aqueous solution of an alkali metal salt of a new aromatic dihydroxy compound such that the new aromatic dihydroxy compound component constitutes 5 to 95 mol % of all aromatic dihydroxy compound components, bringing the obtained mixed aqueous solution into contact with chlorinated hydrocarbon and reacting the resulting solution with phosgene in accordance with an interfacial polymerization process.

(15) A method for collecting an aromatic dihydroxy compound which comprises adding an acid aqueous solution to the aqueous solution phase obtained by the separation/collection step of the above (1) and collecting a deposited aromatic dihydroxy compound as a solid.

(16) The method of the above (15), comprising adding a chlorinated hydrocarbon solvent and an acid aqueous solution to the aqueous solution phase and collecting a deposited aromatic dihydroxy compound as a solid.

(17) The method of the above (15), comprising rinsing the solid aromatic dihydroxy compound collected by the method of the above (15) with a chlorinated hydrocarbon solvent, water or a mixture of these solvents at least once.

Hereinafter, the method of the present invention will be further described.

The waste aromatic polycarbonate used in the present invention may be one produced by a known process such as interfacial polymerization or melt polymerization and has a viscosity average molecular weight of preferably 1,000 to 100,000. The form of the waste aromatic polycarbonate is not particularly limited and is typified by powder, pellets, a sheet, a film and a molded article. For example, in the case of optical disks such as CD, CD-R and DVD, waste optical disks discarded as abandoned products or as waste products such as those which are defectively molded during the production process of optical disks can be used as they are or after a print film and a metal film are peeled and removed. Further, the waste aromatic polycarbonate used may be a solid obtained by removing a solvent from a polycarbonate solution which has not been powdered or pelletized because it has not reached a target molecular weight during production of a polycarbonate and drying the residue. The viscosity average molecular weight (M) of the polycarbonate is determined by substituting specific viscosity ($\eta_{sp}$) determined from a solution prepared by dissolving 0.7 g of the polycarbonate in 100 ml of dichloromethane (methylene chloride) at 20° C. into the following expression.

$$\eta_{sp}/c=[\eta]+0.45\times[\eta]^2 c ([\eta] \text{ is intrinsic viscosity})[\eta]= 1.23\times10^{-4} M^{0.83} c=0.7$$

The polycarbonate may be a polycarbonate which is generally known as an aromatic polycarbonate, for example, a polycarbonate produced from one or a mixture of two or more of dihydroxy compounds such as hydroquinone, resorcinol, 4,4'-dihydroxydiphenyl, 1,4-dihydroxynaphthalene, bis(4-hydroxyphenyl)methane, bis{(4-hydroxy-3,5-dimethyl)phenyl}methane, 1,1-bis(4-hydroxyphenyl)ethane, 1,1-bis(4-hydroxyphenyl)-1-phenylethane, 2,2-bis(4-hydroxyphenyl)propane (commonly known as bisphenol A), 2,2-bis{(4-hydroxy-3-methyl)phenyl}propane, 2,2-bis{(4-hydroxy-3,5-dimethyl)phenyl}propane, 2,2-bis{(3,5-dibromo-4-hydroxy)phenyl}propane, 2,2-bis{(3-isopropyl-4-hydroxy)phenyl}propane, 2,2-bis{(4-hydroxy-3-phenyl)phenyl}propane, 2,2-bis(4-hydroxyphenyl)butane, 2,2-bis(4-hydroxyphenyl)-3-methylbutane, 2,2-bis(4-hydroxyphenyl)-3,3-dimethylbutane, 2,4-bis(4-hydroxyphenyl)-2-methylbutane, 2,2-bis(4-hydroxyphenyl)pentane, 2,2-bis(4-hydroxyphenyl)-4-methylpentane, 1,1-bis(4-hydroxyphenyl)cyclohexane, 1,1-bis(4-hydroxyphenyl)-4-isopropylcyclohexane, 1,1-bis(4-hydroxyphenyl)-3,3,5-trimethylcyclohexane, 9,9-bis(4-hydroxyphenyl)fluorene, 9,9-bis{(4-hydroxy-3-methyl)phenyl}fluorene, α,α'-bis(4-hydroxyphenyl)-o-diisopropylbenzene, α,α'-bis(4-hydroxyphenyl)-m-diisopropylbenzene, α,α'-bis(4-hydroxyphenyl)-p-diisopropylbenzene, 1,3-bis(4-hydroxyphenyl)-5,7-dimethyladamantane, 4,4'-dihydroxydiphenyl sulfone, 4,4'-dihydroxydiphenyl sulfoxide, 4,4'-dihydroxydiphenyl sulfide, 4,4'-dihydroxydiphenyl ketone, 4,4'-dihydroxydiphenyl ether and 4,4'-dihydroxydiphenyl ester.

Of these, a polycarbonate produced from bisphenol A or from a dihydroxy compound comprising bisphenol A as a main component is the most suitable. Hereinafter, "aromatic polycarbonate" may be simply referred to as "polycarbonate".

Further, the polycarbonate may contain a terminal blocking agent at the molecular terminal, and a monohydric phenol compound is preferably used as the terminal blocking agent (molecular weight modifier). For example, phenols such as phenol, p-cresol, p-ethylphenol, p-isopropylphenol, p-tert-butylphenol, p-cumylphenol, p-cyclohexylphenol, p-octylphenol, p-nonylphenol, 2,4-xylenol, p-methoxyphenol, p-hexyloxylphenol, p-decyloxylphenol, o-chlorophenol, m-chlorophenol, p-chlorophenol, p-bromophenol, pentabromophenol, pentachlorophenol, p-phenylphenol, p-isoprepenylphenol, 2,4-di(1'-methyl-1'-phenylethyl)phenol, β-naphthol, α-naphthol, p-(2',4',4'-trimethylchromanyl)phenol, and 2-(4'-methoxyphenyl)-2-(4"-hydroxyphenyl)propane are used alone or in admixture of two or more.

In the method of the present invention, first, a solid polycarbonate (PC) is dissolved in chlorinated hydrocarbon solvent to prepare a solution. In this dissolution step, the kind and amount of the solvent are important factors for conducting the decomposition reaction of the polycarbonate effectively in the subsequent decomposition step.

The chlorinated hydrocarbon is preferably capable of dissolving the polycarbonate satisfactorily and stable in the subsequent decomposition step. As a specific example of the chlorinated hydrocarbon, at least one solvent selected from the group consisting of dichloromethane (methylene chloride), dichloroethane and chloroform is suitable, and dichloromethane is particularly suitable. Hereinafter, these may be simply referred to as organic solvents. These organic solvents are good solvents for a polycarbonate, are actually used as reaction solvents in a polycarbonate production process and cause no adverse effects on polycarbonate production even if remaining in a decomposed and separated aromatic dihydroxy compound. A chlorinated hydrocarbon containing at least one solvent selected from the group consisting of dichloromethane (methylene chloride), dichloroethane and chloroform in an amount of at least 80 wt %, suitably at least 90 wt %, is used as the organic solvent.

The solvent is used in such an amount that the concentration of the polycarbonate (PC) in the solution having the polycarbonate dissolved therein is 8 to 30 wt %, preferably 10 to 28 wt %. When the concentration of the polycarbonate is lower than this range, the rate of the decomposition reaction becomes low and the decomposition reaction time becomes long in the subsequent decomposition step, and disadvantages are caused by using the solvent in large quantity. Meanwhile, when the concentration of the polycarbonate in the solution is too high, time required for dissolution becomes long, and it becomes difficult to cause the decomposition reaction to proceed effectively. Although the temperature at which the solution is prepared is not particularly limited, it is desirably in nearly the same range as that of the reaction temperature in the subsequent decomposition step, i.e. 30 to 50° C.

When a given amount of the polycarbonate is dissolved in the organic solvent, impurities insoluble in the organic solvent, such as additives, a metal film, a coating agent, a print film and a filler which are contained in the polycarbonate molded article exist in the organic solvent. Such insoluble impurities are desirably removed by filtration.

When the decomposition reaction is conducted without removing the impurities, these impurities may be decomposed. When decomposed products of the impurities are mixed into the alkali metal salt aqueous solution of the aromatic dihydroxy compound and the aqueous solution is used in the polycarbonate production process with the decomposed products contained therein, the quality of a polycarbonate which is a product may be adversely affected. Thus, the insoluble materials are preferably removed in advance.

The organic solvent solution of the polycarbonate prepared in the above dissolution step is transferred to the subsequent decomposition step. In the decomposition step, an alkali metal hydroxide is used as a decomposer for the polycarbonate. Illustrative examples of the alkali metal hydroxide include sodium hydroxide and potassium hydroxide. Sodium hydroxide is particularly preferred.

The alkali metal hydroxide is used in the form of an aqueous solution. The concentration of the alkali metal hydroxide in the aqueous solution is preferably 45 to 55 wt %, particularly preferably 47 to 53 wt %. When it is lower than 45 wt %, the decomposition rate becomes low, while when it is higher than 55 wt %, the alkali metal hydroxide is deposited and the aqueous solution is liable to become slurry. When it becomes slurry, the reaction may slow down.

A preferred amount of the alkali metal hydroxide aqueous solution is determined based on the amount of carbonate linkages in the polycarbonate. That is, the metal hydroxide aqueous solution is preferably used in such an amount that it contains 4 to 8 moles of the alkali metal hydroxide per mole of the carbonate linkage of the polycarbonate. When the amount of the alkali metal hydroxide is smaller than 4 moles, the decomposition reaction proceeds very slowly, while when it is larger than 8 moles, costs become high and the amount of an acid aqueous solution used in isolating and collecting an aromatic dihydroxy compound becomes large, which are not preferred from an economical standpoint.

In the decomposition step of the present invention, the temperature at which the decomposition reaction is conducted is preferably 30 to 50° C., more preferably 30 to 45° C. When it is lower than 30° C., the decomposition reaction time becomes long, and processing efficiency may be significantly low. Meanwhile, when it is too high, a large quantity of energy is required for heating, and the color of the solution is liable to become brown during decomposition, so that an aqueous solution of an alkali metal salt of a high-quality dihydroxy compound may not be obtained. Further, the reaction at temperatures not lower than the boiling point of the solvent requires a pressure vessel and requires high equipment costs, which are disadvantageous from an economical standpoint.

Since the alkali metal salt of the aromatic dihydroxy compound produced in the decomposition reaction is liable to be oxidized under a basic condition, it is preferred to add an antioxidant in the reaction solution. Further, it is also effective to reduce the concentration of oxygen in the decomposition step by inert gas. It is particularly desirable to carry out the decomposition step in a non-oxygen atmosphere.

Illustrative examples of the antioxidant include sodium bisulfite ($Na_2S_2O_5$), sodium sulfite ($Na_2SO_3$) and hydrosulfite sodium ($Na_2S_2O_4$). These may be used alone or in admixture of two or more. The antioxidant is preferably used in an amount of 0.05 to 4.0 parts by weight based on 100 parts by weight of the polycarbonate. When its amount is 0.05 to 4.0 parts by weight, an oxidation inhibiting effect is developed, it is advantageous in view of costs, and the decomposition reaction rate does not decrease advantageously.

Illustrative examples of the inert gas include nitrogen and argon. Nitrogen is advantageous and preferred in view of costs.

The decomposition of the polycarbonate in the decomposition step of the present invention is an interfacial reaction in which the polycarbonate dissolved in or swollen by the organic solvent is agitated together with the alkali metal hydroxide aqueous solution, contacts with the aqueous solution at the interface and is decomposed. This reaction is irreversible, carbonate linkages in the polycarbonate are broken, and the polycarbonate is decomposed into an alkali metal salt of a dihydroxy compound and an alkali metal carbonate.

In the decomposed solution thus obtained in the decomposition step, the alkali metal salt of the hydroxy compound and the alkali metal carbonate exist mostly as solids. Therefore, the decomposed solution is slurry. Although the decomposition step may be carried out in the same vessel as that used in the dissolution step, the steps may be carried out in different vessels.

To the decomposed solution (slurry) obtained in the decomposition step, water is added and agitated to dissolve the solids. This step is refereed to as a re-dissolution step to differentiate it from the first dissolution step. The amount of water added in this re-dissolution step is at least an amount in which the solids are dissolved completely. When water is added too much, the concentration of the alkali metal salt of the dihydroxy compound in the aqueous solution decreases, and a decrease in the reaction rate and an increase in costs for distillation of waste solution occur in the next polycarbonate production process. Thus, the amount of water is preferably the minimum amount in which the solids can be dissolved completely.

When water is added to the decomposed solution and agitated in the re-dissolution step, the solids are dissolved in water, and an organic solvent phase and an aqueous solution phase (aqueous phase) in which the alkali metal salt of the hydroxy compound is mainly dissolved are formed. Thus, the processed solution in the re-dissolution step is left to stand to form two phases, i.e. the organic solvent solution phase (organic phase) and the aqueous solution phase (aqueous phase). In this two phase formation step, the two phases are formed simply by leaving the processed solution to stand.

Then, the aqueous solution phase formed in the two phase formation step is separated and collected. That is, the organic phase as the heavy phase obtained in the two phase formation step may be removed from below, or the aqueous solution phase as the light phase may be collected from above. In the aqueous solution phase obtained in this separation/collection step, the alkali metal salt of the dihydroxy compound is contained as an aqueous solution.

The two phases obtained in the above two phase formation step are separated by a liquid-liquid separator such as a decanter to collect the aqueous solution phase (aqueous phase), and this collected aqueous solution containing the alkali metal salt of the dihydroxy compound can be used in the polycarbonate production process as it is. However, if separation of the aqueous phase in the liquid-liquid separator is not sufficient, the organic phase suspended or dispersed in the aqueous phase in particulate form enters the next step and affects a product. Thus, it is preferred to remove the organic phase in the aqueous phase as much as possible by bringing the aqueous phase into contact with new chlorinated hydrocarbon again. To this end, known methods such as contact by a cleaning column, an agitator, separation by a liquid-liquid separator and a centrifugal separator can be used. In particular, a method of bringing the aqueous phase and chlorinated hydrocarbon into countercurrent contact with each other is preferably employed because the organic phase in the aqueous phase can be removed efficiently.

It is also possible that the aqueous solution of the alkali metal salt of the dihydroxy compound obtained by decomposing the waste polycarbonate and a newly prepared aqueous solution of an alkali metal salt of a new dihydroxy compound are mixed together in a given ratio and used in the polycarbonate production process. In that case, the proportion of the new dihydroxy compound is preferably 5 to 95 mol % of all hydroxy compounds.

Further, it is also possible that acid is added to the aqueous solution of the alkali metal salt of the dihydroxy compound obtained by decomposing the waste polycarbonate to deposit, isolate and collect the dihydroxy compound. By depositing and collecting the dihydroxy compound as solids, an aromatic dihydroxy compound raw material having higher purity (e.g. a purity of 99.5% or higher) than a method using the above aqueous solution in the aromatic polycarbonate production process can be obtained.

A suitable method for depositing the aromatic dihydroxy compound is a method of adding an acid aqueous solution to a granulator in which the aqueous solution of the alkali metal salt of the aromatic dihydroxy compound is being agitated and/or circulated in the presence or absence of an organic solvent comprising chlorinated hydrocarbon. By the method, an aromatic dihydroxy compound insoluble in the aqueous phase and the organic phase is obtained as slurry, and the aromatic dihydroxy compound can be obtained by filtrating this slurry. In this case, the final pH of the aqueous phase is preferably 4 to 10, more preferably 6 to 8.5.

The kind of acid in the acid aqueous solution used is not particularly limited. Inorganic acids such as hydrochloric acid, sulfuric acid and phosphoric acid are preferably used.

Illustrative examples of means for filtrating the dihydroxy compound obtained as solids include a strainer, a centrifugal separator, and a centrifugal settler. The centrifugal separator is preferred since the liquid content of the filtered dihydroxy compound is low.

The dihydroxy compound obtained by the above method is unpurified and contains impurities other than the aromatic dihydroxy compound which have been present in the aqueous phase and the organic phase, e.g. additives such as a terminal blocking agent and a colorant for a molded article, a polycarbonate-derived carbonate and a neutral salt resulting from a reaction of the metal hydroxide with the acid aqueous solution. These impurities can be removed by contacting and cleaning the dihydroxy compound with pure water and chlorinated hydrocarbon. Thereby, the purity of the dihydroxy compound can be improved.

To clean the dihydroxy compound, there can be used a method comprising transferring the solid dihydroxy compound to an agitator, adding water and chlorinated hydrocarbon simultaneously or separately and agitating and filtering the solution or a method comprising sprinkling water and chlorinated hydrocarbon on the solid dihydroxy compound in a centrifugal separator simultaneously or separately to rinse it and removing liquid from the compound by centrifugal separation.

The solid aromatic dihydroxy compound collected by the method of the present invention can be reused in an aromatic polycarbonate production process. To reuse the dihydroxy compound, it can be used as it is in a melt polymerization process, and in an interfacial polymerization process, it can be dissolved in an alkali metal hydroxide aqueous solution at desired concentration and used as a raw material for a polycarbonate. In that case, it is also preferred to use a residue resulting from evaporating the remaining organic solvent by heating the solution prepared by dissolving the dihydroxy compound in the alkali metal hydroxide aqueous solution.

Further, it is also possible to use a mixture of the collected dihydroxy compound and a new dihydroxy compound in production of the polycarbonate. In that case, the proportion of the new dihydroxy compound is preferably 5 to 95 mol % of all dihydroxy compounds. The collected aromatic dihydroxy compound and the new aromatic dihydroxy compound may be mixed together in the form of solids, a solid and a liquid, or liquids.

The polycarbonate obtained by using the dihydroxy compound collected by the present invention can be used with modifiers such as a thermal stabilizer, antioxidant, mold releasing agent (e.g. a fatty acid ester), lubricant, plasticizer, antistatic agent, brightening agent, ultraviolet absorber, anti-weathering agent, antimicrobial agent, pigment, dye, filler, toughening agent, other resins and polymers such as rubber and flame retardant added as appropriate.

As the thermal stabilizer, a phosphorus-based thermal stabilizer is preferably used. Illustrative examples thereof include phosphorous acid, phosphoric acid, phosphonous acid, phosphonic acid, and esters thereof. To be more specific, tris(nonylphenyl)phosphite, tris(2,4-di-tert-butylphenyl) phosphite, tris(2,6-di-tert-butylphenyl)phosphite, and tetrakis(2,4-di-tert-butylphenyl) 4,4'-biphenylenediphosphinate are preferably used. These can be used alone or in admixture of two or more. The amount of the thermal stabilizer is preferably 0.001 to 0.1 parts by weight, more preferably 0.002 to 0.05 parts by weight, based on 100 parts by weight of the polycarbonate.

The above thermal stabilizer may be added to the polycarbonate by a method of adding it to the polycarbonate solution after the polymerization reaction or a method of adding it to the polycarbonate powder. In particular, the method of adding the thermal stabilizer to the polycarbonate solution after the polymerization reaction is preferred because the color and thermal stability of the polycarbonate obtained are further improved. A method of adding the thermal stabilizer to the polycarbonate solution after purification or a method of adding the thermal stabilizer to hot water upon granulation by hot water is preferred. The thermal stabilizer may be added as it is or after dissolved in a solvent.

Thus, a suitable embodiment of the present invention is a method for producing a polycarbonate suited for production of an optical disk from an optical disk or defective product produced during production of the optical disks. That is, according to the present invention, there is provided a polycarbonate production method comprising decomposing an optical disk formed from an aromatic polycarbonate or a defective product produced during production of the optical disks by use of an alkali metal hydroxide aqueous solution to obtain an alkali metal salt aqueous solution of an aromatic dihydroxy compound which constitutes the aromatic polycarbonate and producing a polycarbonate by use of the aqueous solution in accordance with interfacial polymerization. The polycarbonate production method comprises the following steps (a) to (f):

(a) a step (dissolution step) of dissolving an optical disk or a defective product produced during production of the optical disks in a chlorinated hydrocarbon solvent to prepare an organic solvent solution having a polycarbonate (PC) dissolved therein in a concentration of 8 to 30 wt %, and to remove impurities remaining therein as required, (b) a step (decomposition step) of adding an alkali metal hydroxide aqueous solution containing 45 to 55 wt % of alkali metal hydroxide to the obtained organic solvent solution to decompose the aromatic polycarbonate at a temperature of 30 to 50° C., (c) a step (re-dissolution step) of adding water to the decomposed solution obtained in the step (b) to dissolve an alkali metal salt of an aromatic dihydroxy compound as a solid contained in the decomposed solution in water, (d) a step (two phase formation step) of leaving the treated solution obtained in the step (c) to stand to form an organic solvent solution phase (organic phase) and an aqueous solution phase (aqueous phase), (e) a step (separation/collection step) of separating the aqueous solution phase (aqueous phase) obtained in the step (d) from the organic solvent solution phase (organic phase) and collecting the aqueous solution phase (aqueous phase), and (f) a step (interfacial polymerization step) of bringing phosgene into contact with the aqueous solution phase obtained in the step (e) or a mixture obtained by mixing this aqueous solution phase with an aqueous solution of an alkali metal salt of a new dihydroxy compound in the presence of a chlorinated hydrocarbon solvent and a basic compound.

The steps (a) to (e) in the above method for producing a polycarbonate from an optical disk or a defective product thereof are virtually the same as those of the above method for obtaining an alkali metal salt aqueous solution of a dihydroxy compound. The chlorinated hydrocarbon solvent and basic compound used in the step (f) are the same as those used in an interfacial polymerization process of polycarbonate. That is, dichloromethane is suitably used as the solvent, and sodium hydroxide or potassium hydroxide is suitably used as the basic compound. In the interfacial polymerization, a reaction accelerator such as an organic amine may be used, and a monofunctional phenol compound (such as p-tert-butylphenol) may be used as a terminal blocking agent.

Since a polycarbonate obtained by the above method has excellent hue and thermal stability, it can be suitably used as a raw material for optical disk substrates such as magneto optical disks, various recordable disks, digital audio disks (so-called compact disks), optical video disks (so-called laser disks) and digital versatile disks (DVD).

EFFECT OF THE INVENTION

According to the present invention, a waste polycarbonate, suitably a waste optical disk (waste disk) can be decomposed in a short time and at low energy cost to collect a dihydroxy compound as an alkali metal aqueous solution, and this aqueous solution can be collected as it is or as a solid dihydroxy compound and used as a raw material for producing a polycarbonate. Thus, the effect of the present invention from an industrial standpoint is significant.

EXAMPLES

Hereinafter, the present invention will be further described with reference to examples. The present invention shall not be limited to these examples in any way. Unless otherwise stated, "parts" indicates "parts by weight". Evaluations were made in the following manners.

(1) Hue (b Value)

Polycarbonate resin pellets were molded into a plate having a size of 50 mm×50 mm and a thickness of 2 mm at a cylinder temperature of 340° C. by use of an injection molding machine (Nikko Anchor V-17-65 of Japan Steel Works, Ltd.). The b value of the molded plate was measured by use of a calorimeter (product of Nippon Denshoku Industries Co., Ltd.).

(2) Thermal Stability (ΔE)

Polycarbonate resin pellets were molded by use of an injection molding machine (Nikko Anchor V-17-65 of Japan Steel Works, Ltd.) at a cylinder temperature of 340° C. to prepare test pieces (plates each having a size of 50 mm×50 mm and a thickness of 2 mm) one of which had been retained for 10 minutes and the other of which had been retained only for 1 minute, and a change in hue (ΔE) between the test pieces was measured. The change in hue was calculated by substituting the L, a and b values measured by a calorimeter (product of Nippon Denshoku Industries Co., Ltd.) of the test pieces into the following expression.

$$\Delta E = [(L'-L)^2 + (a'-a)^2 + (b'-b)^2]^{1/2}$$

(L, a and b are of the test piece without a retention of 10 minutes, and L', a' and b' are of the test piece with a retention of 10 minutes.)

(3) Concentration of Bisphenol A Sodium Salt in Bisphenol A Sodium Salt Aqueous Solution A bisphenol A sodium salt aqueous solution was diluted with a sodium hydroxide aqueous solution such that the concentration of bisphenol A sodium salt became 0.1 to 0.5 wt %, absorbance at a wavelength of 294 nm was measured by an ultraviolet meter, and the concentration of the bisphenol A sodium salt in the aqueous solution was measured by a calibration curve prepared in advance.

(4) Purity of Bisphenol A

By use of high-performance liquid chromatography of Waters Co., Ltd., 1 ml of acetonitrile containing o-cresol as an internal reference was added to 0.2 g of sample (sample in Example 6 was measured after rinsed with pure water) to dissolve the sample, a chromatograph was obtained using an acetonitrile/0.2% acetic acid aqueous solution as a developing solvent, and the purity of bisphenol A was measured by a calibration curve prepared in advance.

(5) Sodium Ion Content of Bisphenol A 10 ml of ultrapure water was added to 1 g of bisphenol A and left to stand for 24 hours to extract ion components. An ion chromatograph of this solution was obtained, and the sodium ion content was determined by a calibration curve prepared in advance.

(6) Block Error Rate (BLER)

Polycarbonate pellets were molded into an aluminum-laminated substrate having a thickness of 1.2 mm and a diameter of 120 mm by means of an injection molding machine (DISK3MIII of Sumitomo Heavy Industries, Ltd.), and the block error rate of the substrate was measured by means of a BLER measuring device (CD player control unit CDS-3000 of Sony Corporation). "$C_1AVE$" used herein refers to the average of C1 errors (random errors that can be corrected by the C1 code) per second. A $C_1AVE$ value of not larger than 1 indicates a satisfactory level.

(7) Haasen Color Number

This was measured in accordance with JIS K-0071.

Example 1

100 parts of commercially available compact disk and 600 parts of methylene chloride were charged into an agitator and agitated for 6 hours. The films of the compact disk were dispersed in the polycarbonate/methylene chloride solution. This solution was passed through a strainer (product of Advantech Co., Ltd.) equipped with a cellulose filter having openings of 10 μm to remove the films (such as a print layer, ultraviolet curable resin and aluminum film) of the compact disk.

To a reactor equipped with a thermometer, agitator, reflux condenser and water bath, 264 parts (dope concentration: 14.2%) of the polycarbonate/methylene chloride solution, 71 parts (6.0 moles per mole of the carbonate linkage of the polycarbonate) of 50% sodium hydroxide aqueous solution and 0.6 parts of hydrosulfite sodium were added and agitated. Then, when the temperature of the water bath was adjusted to 40° C., intense reflux started after 8 minutes, and its intensity ceased after 20 minutes. The reaction was continued at 40° C. for 5 hours. After completion of the 5 hours-reaction, solids were deposited in the reactor. As a result of obtaining and analyzing a part of the solids, the solid comprised a bisphenol A sodium salt and sodium carbonate. The adjustment of the temperature of the water bath was stopped, 337.5 parts of pure water was added, and the solids were dissolved by agitating continuously for 1 hour.

The reaction mixture was transferred to a separating funnel and separated into 455 parts of aqueous phase and 224 parts of organic phase. The aqueous phase was an alkaline aqueous solution and contained bisphenol A, sodium carbonate, sodium hydroxide and p-tert-butylphenol. As for the organic phase, methylene chloride was evaporated and collected by an evaporator, and the residue was discarded. The residue comprised an unreacted polycarbonate and a decomposition product of the additive and weighed 1.1 parts.

After 100 parts of methylene chloride was added to 455 parts of the separated aqueous phase and mixed vigorously, the mixture was left to stand so as to allow it to separate into an aqueous phase and a methylene chloride phase. Methylene chloride was collected by an evaporator. This operation was repeated for three times to obtain a cleaned bisphenol A sodium salt aqueous solution (bisphenol A sodium salt concentration: 76.6 g/L).

Example 2

A bisphenol A sodium salt aqueous solution (bisphenol A sodium salt concentration: 74.7 g/L) was obtained in the same manner as in Example 1 except that 860 parts of methylene chloride was mixed with 100 parts of compact disk and that 360 parts (dope concentration: 10.4%) of the polycarbonate/methylene chloride solution was used.

Example 3

A bisphenol A sodium salt aqueous solution (bisphenol A sodium salt concentration: 75.0 g/L) was obtained in the same manner as in Example 1 except that 56.3 parts (4.8 moles per mole of the carbonate linkage of the polycarbonate) of 50% sodium hydroxide aqueous solution was used.

Example 4

100 parts of waste polycarbonate sheet and 600 parts of methylene chloride were charged into an agitator and agitated for 6 hours. This solution was passed through a strainer (product of Advantech Co., Ltd.) equipped with a cellulose filter having openings of 10 μm to remove foreign materials (such as a sheet protective film, label and dirt stuck on the sheet).

To a reactor equipped with a thermometer, agitator, reflux condenser and water bath, 264 parts (dope concentration: 14.2%) of the polycarbonate/methylene chloride solution, 71 parts (6.0 moles per mole of the carbonate linkage of the polycarbonate) of 50% sodium hydroxide aqueous solution and 0.6 parts of hydrosulfite sodium were added and agitated. Then, when the temperature of the water bath was adjusted to 40° C., intense reflux started after 15 minutes, and its intensity ceased after 30 minutes. The reaction was continued at 40° C. for 5 hours. After completion of the hours-reaction, solids were deposited in the reactor. As a result of obtaining and analyzing a part of the solids, the solid comprised a bisphenol A sodium salt and sodium carbonate. The adjustment of the temperature of the water bath was stopped, 337.5 parts of pure water was added, and the solids were dissolved by agitating continuously for 1 hour.

The reaction mixture was transferred to a separating funnel and left to stand for 1 hour. Thereby, the mixture was separated into 455 parts of aqueous phase and 224 parts of organic phase. The aqueous phase was an alkaline aqueous solution and contained bisphenol A, sodium carbonate, sodium hydroxide and p-tert-butylphenol. As for the organic phase, methylene chloride was evaporated and collected by an evaporator, and the residue was discarded. The residue comprised an unreacted polycarbonate and a decomposition product of the additive and weighed 1.1 parts.

When the concentration of bisphenol A sodium salt in the bisphenol A sodium salt aqueous solution (aqueous phase) was measured, it was 78.2 g/L. Since sufficient separation could not be achieved by leaving the reaction mixture to stand only for 1 hour, the organic phase was dispersed in the bisphenol A sodium salt aqueous solution, and in the dispersed organic phase, organic impurities (such as a surface-hardening film of the sheet, ultraviolet absorber, blue dye, thermal stabilizer and decomposed mold releasing agent) existed.

In a column having an internal diameter of 108.3 mm, a filler IMTP#15 was filled at a filling height of 800 mm, and a dispersion plate was placed in its lower portion. The bisphenol A sodium salt aqueous solution was charged into the column from its lower portion at a flow rate of 500 L/h, and methylene chloride was charged into the column from its upper portion at a flow rate of 60 L/h, thereby bringing them into contact with each other continuously inside the column. A U-shaped tube was placed such that the continuous phase became methylene chloride, and the position of the interface was set. An aqueous solution flown out from the upper portion of the column had been collected since 1 hour after the start of the operation. Thus, a cleaned bisphenol A sodium salt aqueous solution was obtained.

Comparative Example 1

The procedure of Example 1 was repeated except that 975 parts (dope concentration: 3.85%) of solution obtained by dissolving 50 parts of compact disk into 1,250 parts of methylene chloride and filtering the mixture was used in the decomposition reaction. After completion of the 5-hour reaction, an organic phase obtained by separation of the reaction mixture was concentrated, and when its solid content was measured, it was 4.3 parts. Further, a cleaned bisphenol A sodium salt aqueous solution (bisphenol A sodium salt concentration: 70.1 g/L) was obtained.

Comparative Example 2

The procedure of Example 1 was repeated except that 111 parts of 32% sodium hydroxide aqueous solution was used in the decomposition reaction in place of 71 parts of 50% sodium hydroxide aqueous solution. After completion of the 5-hour reaction, an organic phase obtained by separation of the reaction mixture was concentrated, and when its solid content was measured, it was 24.8 parts. Further, a cleaned bisphenol A sodium salt aqueous solution (bisphenol A sodium salt concentration: 25.9 g/L) was obtained. The reaction rate was 34%.

Comparative Example 3

The procedure of Example 1 was repeated except that 89 parts of 40% sodium hydroxide aqueous solution was used in the decomposition reaction in place of 71 parts of 50% sodium hydroxide aqueous solution. After completion of the 5-hour reaction, an organic phase obtained by separation of the reaction mixture was concentrated, and when its solid content was measured, it was 8.2 parts. Further, a cleaned bisphenol A sodium salt aqueous solution (bisphenol A sodium salt concentration: 59.3 g/L) was obtained. The reaction rate was 78%.

Comparative Example 4

The procedure of Example 1 was repeated except that the temperature of the water bath was set at 15° C. and the sodium hydroxide aqueous solution was added dropwise at a rate at which the internal temperature of the reactor was kept at 25° C. at a maximum. The dropwise addition took 1 hour. After completion of the 5-hour reaction, an organic phase obtained by separation of the reaction mixture was concentrated, and when its solid content was measured, it was 412 parts. Further, a cleaned bisphenol A sodium salt aqueous solution (bisphenol A sodium salt concentration: 34.5 g/L) was obtained. The reaction rate was 45%.

Comparative Example 5

37.5 parts of polycarbonate resin pellets for a disk substrate (AD-5503 of Teijin Chemicals Ltd., viscosity average molecular weight: 15,200) and 500 parts of chlorobenzene were charged into an agitator and agitated for 6 hours. The pellets were not completely dissolved in chlorobenzene. Some of them were dissolved, and the rest existed as solids.

To a reactor equipped with a thermometer, agitator, reflux condenser and oil bath, all of the content of the agitator was transferred, and 71 parts (6.0 moles per mole of the carbonate linkage of the polycarbonate) of 50% sodium hydroxide aqueous solution and 0.6 parts of hydrosulfite sodium were added and agitated. Then, when the temperature of the oil bath was adjusted to 100° C., intense reflux started after 80 minutes, and its intensity ceased after 100 minutes. The reaction was continued at 100° C. for 5 hours. After completion of the 5 hours-reaction, solids were deposited in the reactor. As a result of obtaining and analyzing a part of the deposited solids, it comprised a bisphenol A sodium salt and sodium carbonate. The adjustment of the temperature of the oil bath was stopped, 337.5 parts of pure water was added, and the solids were dissolved by agitating continuously for 1 hour.

The reaction mixture was transferred to a separating funnel and separated into 452 parts of aqueous phase and 225 parts of organic phase. The aqueous phase was an alkaline aqueous solution and contained bisphenol A, sodium carbonate, sodium hydroxide and p-tert-butylphenol. As for the organic phase, chlorobenzene was evaporated and collected by an evaporator, and the residue was discarded. The residue comprised an unreacted polycarbonate and a decomposition product of the additive and weighed 0.6 parts.

After 100 parts of methylene chloride was added to 455 parts of the separated aqueous phase and mixed vigorously, the mixture was left to stand so as to allow it to separate into an aqueous phase and a methylene chloride phase. Methylene chloride was collected by an evaporator. This operation was repeated for three times to obtain a cleaned bisphenol A sodium salt aqueous solution (bisphenol A sodium salt concentration: 77.7 g/L). This aqueous solution was colored yellow and had a Haasen color number of 70.

Comparative Example 6

A cleaned bisphenol A sodium salt aqueous solution (bisphenol A sodium salt concentration: 77.8 g/L) was obtained in the same manner as in Comparative Example 5 except that 300 parts of chlorobenzene was used in the decomposition reaction. This aqueous solution was colored yellow and had a Haasen color number of 80.

Example 5

To a vessel equipped with a thermometer, agitator and reflux condenser, 455 parts of the bisphenol A sodium salt aqueous solution obtained in Example 1 was transferred, and 170 parts of methylene chloride was further added and agitated. Under agitation, 36.1 parts of 98% concentrated sulfuric acid was added dropwise in 1 hour by use of a dropping funnel. When agitation was stopped and the inside of the vessel was checked, the content of the vessel was separated in three phases, i.e. an aqueous phase, a methylene chloride phase and deposited bisphenol A.

This slurry was filtered by a centrifugal separator, and in the centrifugal separator being operated, 45 parts of methylene chloride, 45 parts of pure water, 45 parts of methylene chloride and 45 parts of pure water were sprinkled on solids in this order to rinse the solids. When the solids were taken out of the centrifugal separator and dried, they weighed 26.9 parts. The purity of bisphenol A was 99.8%, and the content of sodium ions was 8 ppm.

Example 6

The procedure of Example 5 was repeated except that solids were not rinsed. When the solids were taken out of a centrifugal separator and dried, they weighed 29.9 parts. The purity of bisphenol A was 98.2%, and the content of sodium ions was 1.3%.

Example 7

The procedure of Example 5 was repeated except that 170 parts of methylene chloride was not added. However, when the inside of the vessel was checked after completion of dropwise addition of concentrated sulfuric acid, water slurry free of methylene chloride was formed.

This water slurry was filtered by a centrifugal separator, and in the centrifugal separator being operated, 45 parts of methylene chloride, 45 parts of pure water, 45 parts of methylene chloride and 45 parts of pure water were sprinkled on solids in this order to rinse the solids. When the solids were taken out of the centrifugal separator and dried, they weighed 27.4 parts. The purity of bisphenol A was 99.5%, and the content of sodium ions was 15 ppm.

TABLE 1

| | Dope Concentration (wt %) | Concentration of Sodium Hydroxide Aqueous Solution (wt %) | Sodium Hydroxide per Mole of Carbonate Linkage (mole) | Decomposition Reaction Temperature (° C.) | Reaction Rate (%) | Haasen color number |
|---|---|---|---|---|---|---|
| Ex. 1 | 14.2 | 50 | 6.0 | 40 | 97.1 | 10 |
| Ex. 2 | 10.4 | 50 | 6.0 | 40 | 94.7 | 10 |
| Ex. 3 | 14.2 | 50 | 4.8 | 40 | 92.0 | 10 |
| Ex. 4 | 14.2 | 50 | 6.0 | 40 | 97.1 | 10 |
| C. Ex. 1 | 3.85 | 50 | 6.0 | 40 | 88.8 | 10 |
| C. Ex. 2 | 14.2 | 32 | 6.0 | 40 | 34.0 | 10 |
| C. Ex. 3 | 14.2 | 40 | 6.0 | 40 | 78.1 | 10 |
| C. Ex. 4 | 14.2 | 50 | 6.0 | 15 to 25 | 45.0 | 10 |
| C. Ex. 5 | 7.0 | 50 | 6.0 | 100 | 98.5 | 70 |
| C. Ex. 6 | 11.0 | 50 | 6.0 | 100 | 98.6 | 80 |

Ex.: Example, C. Ex.: Comparative Example

TABLE 2

| | Processing Conditions | | | | |
|---|---|---|---|---|---|
| | Bisphenol A Aqueous Solution Used | Addition of Methylene Chloride | Rinsing | Purity of Bisphenol A (%) | Content of Sodium Ions |
| Ex. 5 | Example 1 | Added | Rinsed | 99.8 | 8 ppm |
| Ex. 6 | Example 1 | Added | Not Rinsed | 98.2 | 1.3% |
| Ex. 7 | Example 1 | Not Added | Rinsed | 99.5 | 15 ppm |

Ex.: Example

Reference Example 1

Production Method of Polycarbonate Resin (A) To a reactor equipped with a thermometer, agitator, reflux condenser and circulator, 650 parts of ion exchange water and 252 parts of 25% sodium hydroxide aqueous solution were added. Then, 170 parts of purchased bisphenol A, 13 parts of methylene chloride and 0.34 parts of hydrosulfite were also added and dissolved in 40 minutes with the temperature kept at 30° C. while circulated to prepare a bisphenol A sodium salt aqueous solution.

(B) To a reactor equipped with a thermometer, agitator and reflux condenser, 367 parts of the bisphenol A sodium salt aqueous solution prepared in (A) and 181 parts of methylene chloride were added, and 28.3 parts of phosgene was blown into the mixture in 40 minutes at 15 to 25° C. under agitation. After completion of feeding of phosgene, 7.2 parts of 48% sodium hydroxide aqueous solution and 2.42 parts of solid p-tert-butylphenol were added to emulsify the mixture, and after 10 minutes, 0.06 parts of triethylamine was added, and the mixture was further agitated at 28 to 33° C. for 1 hour to complete the reaction. After completion of the reaction, 400 parts of methylene chloride was added to and mixed with the product. Then, agitation was stopped to separate an aqueous phase and an organic phase from each other. Thereby, an organic solvent solution having a polycarbonate resin concentration of 14.5 wt % was obtained.

After 150 parts of water was added to the above organic solvent solution and agitated, agitation was stopped to separate an organic phase from an aqueous phase. After 200 parts of hydrochloric acid solution having a pH of 3 was added to this organic phase and agitated and triethylamine and the like were extracted, agitation was stopped to separate an organic phase from an aqueous phase. Then, after 200 parts of ion exchange water was added to the separated organic phase and agitated, agitation was stopped to separate an organic phase from an aqueous phase. This operation was repeated (4 times) until the conductivity of the aqueous phase became nearly the same as that of ion exchange water. The obtained purified polycarbonate resin solution was filtered by use of a filter made of SUS304 and having a filtration accuracy of 1 μm.

Then, the organic solvent solution, together with 100 L of ion exchange water, was charged into a 1000-L kneader having an isolation chamber having a foreign matter outlet at the bearing and having an inner wall made of SUS316L, methylene chloride was evaporated at a water temperature of 42° C. to obtain powder, and a mixture of the powder and water was charged into a hydrothermal treatment tank equipped with an agitator and controlled to a water temperature of 95° C. and agitated for 30 minutes in a mixing ratio of 25 parts of the powder to 75 parts of water. This mixture of the powder and water was separated by a centrifugal separator to obtain powder comprising 0.5 wt % of methylene chloride and 45 wt % of water. This powder was continuously fed into a conductive heat-receiving groove type twin-screw agitated continuous dryer made of SUS316L controlled to 140° C. at 50 kg/h (in terms of polycarbonate resin) and dried for an average drying time of 3 hours to obtain powder.

To 100 parts of this powder, 0.01 parts of tris(2,6-di-tert-butylphenyl)phosphite, 0.01 parts of tetrakis(2,4-di-tert-butylphenyl) 4,4'-biphenylenediphosphinate and 0.08 parts of monoglyceride stearate were added and mixed. Then, the powder was melt-kneaded and melt-extruded from a vented twin-screw extruder [TEM-50B of TOSHIBA MACHINE CO., LTD.] at a cylinder temperature of 280° C. while deaerated by use of a dry vacuum pump at a vent suction pressure of 700 Pa to obtain pellets. The viscosity average molecular weight of the obtained pellets was measured. Further, a disk was molded by use of the pellets, and the block error rate ($C_1$AVE) thereof was measured. The measurement results are shown in Table 3.

Example 8

Pellets were obtained in the same manner as in Reference Example 1 except that 40.5 parts of the bisphenol A sodium salt aqueous solution obtained in Example 1 and 349.3 parts of the aqueous solution prepared in Reference Example 1 were mixed and used as a bisphenol A sodium salt aqueous solution. The viscosity average molecular weight of the obtained pellets was measured. Further, a disk was molded by use of the pellets, and the block error rate ($C_1$AVE) thereof was measured. The measurement results are shown in Table 3.

Example 9

Pellets were obtained in the same manner as in Reference Example 1 except that a bisphenol A sodium salt aqueous solution was prepared by using the collected bisphenol A obtained in Example 5 in place of the purchased bisphenol A. The viscosity average molecular weight of the obtained pellets was measured. Further, a disk was molded by use of the pellets, and the block error rate ($C_1$AVE) thereof was measured. The measurement results are shown in Table 3.

Example 10

Pellets were obtained in the same manner as in Reference Example 1 except that a bisphenol A sodium salt aqueous solution was prepared by using the collected bisphenol A obtained in Example 6 in place of the purchased bisphenol A. The viscosity average molecular weight of the obtained pellets was measured. Further, a disk was molded by use of the pellets, and the block error rate ($C_1$AVE) thereof was measured. The measurement results are shown in Table 3.

Example 11

Pellets were obtained in the same manner as in Reference Example 1 except that a bisphenol A sodium salt aqueous solution was prepared by using the collected bisphenol A obtained in Example 7 in place of the purchased bisphenol A. The viscosity average molecular weight of the obtained pellets was measured. Further, a disk was molded by use of the pellets, and the block error rate ($C_1$AVE) thereof was measured. The measurement results are shown in Table 3.

Example 12

Pellets were obtained in the same manner as in Reference Example 1 except that a bisphenol A sodium salt aqueous solution was prepared by using a mixture comprising the collected bisphenol A obtained in Example 5 and the purchased bisphenol A in a ratio of 5:95 in place of the purchased bisphenol A. The viscosity average molecular weight of the obtained pellets was measured. Further, a disk was molded by use of the pellets, and the block error rate ($C_1AVE$) thereof was measured. The measurement results are shown in Table 3.

TABLE 3

| | Bisphenol A Used | Viscosity Average Molecular Weight | $C_1AVE$ |
|---|---|---|---|
| R. Ex. 1 | Purchased Product | 15200 | 0.55 |
| Ex. 8 | Bisphenol A in Ex. 1:Purchased Product = 5:95 | 15100 | 0.82 |
| Ex. 9 | Bisphenol A in Ex. 5 | 15100 | 0.51 |
| Ex. 10 | Bisphenol A in Ex. 6 | 15200 | 0.75 |
| Ex. 11 | Bisphenol A in Ex. 7 | 14800 | 0.88 |
| Ex. 12 | Bisphenol A in Ex. 5:Purchased Product = 5:95 | 15200 | 0.54 |

Ex.: Example, R. Ex.: Reference Example

Reference Example 2

Production Method of Polycarbonate Resin (A) To a reactor equipped with a thermometer, agitator, reflux condenser and circulator, 650 parts of ion exchange water and 252 parts of 25% sodium hydroxide aqueous solution were added. Then, 170 parts of purchased bisphenol A, 13 parts of methylene chloride and 0.34 parts of hydrosulfite were also added and dissolved in 40 minutes with the temperature kept at 30° C. while circulated to prepare a bisphenol A sodium salt aqueous solution.

(B) To a reactor equipped with a thermometer, agitator and reflux condenser, 367 parts of the bisphenol A sodium salt aqueous solution prepared in (A) and 181 parts of methylene chloride were added, and 28.3 parts of phosgene was blown into the mixture in 40 minutes at 15 to 25° C. under agitation. After completion of feeding of phosgene, 7.2 parts of 48% sodium hydroxide aqueous solution and 1.55 parts of solid p-tert-butylphenol were added to emulsify the mixture, and after 10 minutes, 0.06 parts of triethylamine was added, and the mixture was further agitated at 28 to 33° C. for 1 hour to complete the reaction. After completion of the reaction, 400 parts of methylene chloride was added to and mixed with the product. Then, agitation was stopped to separate an aqueous phase and an organic phase from each other. Thereby, an organic solvent solution having a polycarbonate resin concentration of 14.5 wt % was obtained.

After 150 parts of water was added to the above organic solvent solution and agitated, agitation was stopped to separate an organic phase from an aqueous phase. After 200 parts of hydrochloric acid solution having a pH of 3 was added to this organic phase and agitated and triethylamine and the like were extracted, agitation was stopped to separate an organic phase from an aqueous phase. Then, after 200 parts of ion exchange water was added to the separated organic phase and agitated, agitation was stopped to separate an organic phase from an aqueous phase. This operation was repeated (4 times) until the conductivity of the aqueous phase became nearly the same as that of ion exchange water. The obtained purified polycarbonate resin solution was filtered by use of a filter made of SUS304 and having a filtration accuracy of 1 μm.

Then, the organic solvent solution, together with 100 L of ion exchange water, was charged into a 1000-L kneader having an isolation chamber having a foreign matter outlet at the bearing and having an inner wall made of SUS316L, methylene chloride was evaporated at a water temperature of 42° C. to obtain powder, and a mixture of the powder and water was charged into a hydrothermal treatment tank equipped with an agitator controlled to a water temperature of 95° C. and agitated for 30 minutes in a mixing ratio of 25 parts of the powder to 75 parts of water. This mixture of the powder and water was separated by a centrifugal separator to obtain powder comprising 0.5 wt % of methylene chloride and 45 wt % of water. This powder was continuously fed into a conductive heat-receiving groove type twin-screw agitated continuous dryer made of SUS316L controlled to 140° C. at 50 kg/h (in terms of polycarbonate resin) and dried for an average drying time of 3 hours to obtain powder.

To 100 parts of this powder, 0.01 parts of tris(2,6-di-tert-butylphenyl)phosphite, 0.01 parts of tetrakis(2,4-di-tert-butylphenyl) 4,4'-biphenylenediphosphinate and 0.08 parts of monoglyceride stearate were added and agitated. Then, the powder was melt-kneaded and melt-extruded from a vented twin-screw extruder [TEM-50B of TOSHIBA MACHINE CO., LTD.] at a cylinder temperature of 280° C. while deaerated by use of a dry vacuum pump at a vent suction pressure of 700 Pa to obtain pellets. The viscosity average molecular weight of the obtained pellets was measured. Further, the pellets were molded, and the hue (b value) and thermal stability (ΔE) thereof were evaluated. The results are shown in Table 4.

Example 13

Pellets were obtained in the same manner as in Reference Example 2 except that 40.5 parts of the bisphenol A sodium salt aqueous solution obtained in Example 1 and 349.3 parts of the aqueous solution prepared in Reference Example 2 were mixed and used as a bisphenol A sodium salt aqueous solution. The viscosity average molecular weight of the obtained pellets was measured. Further, the pellets were molded, and the hue (b value) and thermal stability (ΔE) thereof were evaluated. The results are shown in Table 4.

Example 14

Pellets were obtained in the same manner as in Reference Example 2 except that a bisphenol A sodium salt aqueous solution was prepared by using the collected bisphenol A obtained in Example 5 in place of the purchased bisphenol A. The viscosity average molecular weight of the obtained pellets was measured. Further, the pellets were molded, and the hue (b value) and thermal stability (ΔE) thereof were evaluated. The results are shown in Table 4.

Example 15

Pellets were obtained in the same manner as in Reference Example 2 except that a bisphenol A sodium salt aqueous solution was prepared by using the collected bisphenol A obtained in Example 6 in place of the purchased bisphenol A. The viscosity average molecular weight of the obtained pellets was measured. Further, the pellets were molded, and the hue (b value) and thermal stability (ΔE) thereof were evaluated. The results are shown in Table 4.

Example 16

Pellets were obtained in the same manner as in Reference Example 2 except that a bisphenol A sodium salt aqueous solution was prepared by using the collected bisphenol A obtained in Example 7 in place of the purchased bisphenol A. The viscosity average molecular weight of the obtained pellets was measured. Further, the pellets were molded, and the hue (b value) and thermal stability (ΔE) thereof were evaluated. The results are shown in Table 4.

Example 17

Pellets were obtained in the same manner as in Reference Example 2 except that a bisphenol A sodium salt aqueous solution was prepared by using a mixture comprising the collected bisphenol A obtained in Example 5 and the purchased bisphenol A in a ratio of 5:95 in place of the purchased bisphenol A. The viscosity average molecular weight of the obtained pellets was measured. Further, the pellets were molded, and the hue (b value) and thermal stability (ΔE) thereof were evaluated. The results are shown in Table 4.

Comparative Example 7

Pellets were obtained in the same manner as in Reference Example 2 except that 40.5 parts of the bisphenol A sodium salt aqueous solution obtained in Comparative Example 5 and 349.3 parts of the aqueous solution prepared in Reference Example 2 were mixed and used as a bisphenol A sodium salt aqueous solution. The viscosity average molecular weight of the obtained pellets was measured. Further, the pellets were molded, and the hue (b value) and thermal stability (ΔE) thereof were evaluated. The results are shown in Table 4.

Comparative Example 8

Pellets were obtained in the same manner as in Reference Example 2 except that 40.5 parts of the bisphenol A sodium salt aqueous solution obtained in Comparative Example 6 and 349.3 parts of the aqueous solution prepared in Reference Example 2 were mixed and used as a bisphenol A sodium salt aqueous solution. The viscosity average molecular weight of the obtained pellets was measured. Further, the pellets were molded, and the hue (b value) and thermal stability (ΔE) thereof were evaluated. The results are shown in Table 4.

TABLE 4

| | Bisphenol A Used | Viscosity Average Molecular Weight | b Value of Pellets | ΔE |
|---|---|---|---|---|
| R. Ex. 2 | Purchased Product | 23500 | 3.0 | 0.11 |
| Ex. 13 | Bisphenol A in Ex. 1:Purchased Product = 5:95 | 23400 | 3.1 | 0.12 |
| Ex. 14 | Bisphenol A in Ex. 5 | 23500 | 3.0 | 0.11 |
| Ex. 15 | Bisphenol A in Ex. 6 | 23100 | 3.3 | 0.19 |
| Ex. 16 | Bisphenol A in Ex. 7 | 23400 | 3.2 | 0.12 |
| Ex. 17 | Bisphenol A in Ex. 5:Purchased Product = 5:95 | 23500 | 3.0 | 0.11 |
| C. Ex. 7 | Bisphenol A in C. Ex. 5:Purchased Product = 5:95 | 23400 | 4.2 | 0.21 |
| C. Ex. 8 | Bisphenol A in C. Ex. 6:Purchased Product = 5:95 | 23500 | 4.2 | 0.20 |

Ex.: Example, R. Ex.: Reference Example, C. Ex.: Comparative Example

The invention claimed is:

1. A method for obtaining an alkali metal salt aqueous solution of an aromatic dihydroxy compound which constitutes a waste aromatic polycarbonate by decomposing the aromatic polycarbonate by an alkali metal hydroxide aqueous solution, the method comprising:

(a) a step (dissolution step) of dissolving a waste aromatic polycarbonate in a chlorinated hydrocarbon solvent to prepare an organic solvent solution having the aromatic polycarbonate (PC) dissolved therein in a concentration of 8 to 30 wt%, (b) a step (decomposition step) of reacting the obtained organic solvent solution with an alkali metal hydroxide aqueous solution containing 45 to 55 wt% of alkali metal hydroxide at a temperature of 30 to 50° C. to decompose the aromatic polycarbonate, (c) a step (re-dissolution step) of adding water to the decomposed solution obtained in the step (b) to dissolve an alkali metal salt of an aromatic dihydroxy compound as a solid contained in the decomposed solution in water, (d) a step (two phase formation step) of leaving the treated solution obtained in the step (c) to stand to form an organic solvent solution phase (organic phase) and an aqueous solution phase (aqueous phase), (e) a step (separation/collection step) of separating the aqueous solution phase (aqueous phase) formed in the step (d) from the organic solvent solution phase (organic phase) and collecting the aqueous solution phase (aqueous phase), and (g) a step (re-separation/collection step) of adding a chlorinated hydrocarbon solvent to the aqueous solution phase obtained by the separation/collection step to form an organic solvent phase and an aqueous solution phase, separating the aqueous solution phase from the organic solvent phase and collecting the obtained aqueous solution phase.

2. The method of claim 1, wherein the chlorinated hydrocarbon solvent contains at least one solvent selected from the group consisting of dichloromethane, dichloroethane and chloroform in an amount of at least 80 wt%.

3. The method of claim 1, wherein the alkali metal hydroxide is sodium hydroxide.

4. The method of claim 1, wherein the aromatic polycarbonate comprises bisphenol A as a main aromatic dihydroxy compound.

5. The method of claim 1, wherein the organic solvent solution in the dissolution step has the aromatic polycarbonate (PC) dissolved therein in a concentration of 10 to 28 wt%.

6. The method of claim 1, wherein the alkali metal hydroxide aqueous solution in the decomposition step is an aqueous solution containing 47 to 53 wt% of alkali metal hydroxide.

7. The method of claim 1, wherein in the decomposition step, the alkali metal hydroxide aqueous solution is used in such an amount that it contains 4 to 8 moles of alkali metal hydroxide per mole of the carbonate linkage of the aromatic polycarbonate.

8. The method of claim 1, wherein in the decomposition step, the decomposition temperature is a temperature of 30 to 45° C.

9. The method of claim 1, wherein the waste polycarbonate is an optical disk product formed from a polycarbonate or a material discharged from its production process.

10. The method of claim 1, wherein in the dissolution step, an antioxidant is added to the organic solvent solution in an amount of 0.05 to 4 parts by weight based on 100 parts by weight of the aromatic polycarbonate.

11. The method of claim 1, wherein the decomposition step, re-dissolution step and two phase formation step are carried out at least in a non-oxygen gas atmosphere.

12. A method for producing an aromatic polycarbonate which comprises bringing the aqueous solution phase obtained by the separation/collection step of claim 1 into contact with chlorinated hydrocarbon and reacting the phase with phosgene in accordance with an interfacial polymerization process.

13. A method for producing an aromatic polycarbonate which comprises mixing the aqueous solution phase obtained by the separation/collection step of claim 1 with an aqueous solution of an alkali metal salt of a new aromatic dihydroxy compound such that the new aromatic dihydroxy compound component constitutes 5 to 95 mol% of all aromatic dihydroxy compound components, bringing the obtained mixed aqueous solution into contact with chlorinated hydrocarbon and reacting the resulting solution with phosgene in accordance with an interfacial polymerization process.

14. A method for collecting an aromatic dihydroxy compound which comprises adding an acid aqueous solution to the aqueous solution phase obtained by the separation/collection step of claim 1 and collecting a deposited aromatic dihydroxy compound as a solid.

15. The method of claim 14, comprising adding a chlorinated hydrocarbon solvent and an acid aqueous solution to the aqueous solution phase and collecting a deposited aromatic dihydroxy compound as a solid.

16. The method of claim 14, comprising rinsing the solid aromatic dihydroxy compound collected by the method of claim 15 with a chlorinated hydrocarbon solvent, water or a mixture of these solvents at least once.

* * * * *